US012213686B2

(12) United States Patent
Gogarty et al.

(10) Patent No.: US 12,213,686 B2
(45) Date of Patent: Feb. 4, 2025

(54) KNEE ARTHROPLASTY VALIDATION AND GAP BALANCING INSTRUMENTATION

(71) Applicant: Orthosoft ULC, Montreal (CA)

(72) Inventors: Emily Gogarty, Montreal (CA); Pierre Couture, Montreal (CA); Adam H. Sanford, Minneapolis, MN (US); Frederique DesbiensBlais, Montreal (CA); Marc-Antoine Dufour, Montreal (CA); Vincent Pelletier, Montreal (CA); Yann Facchinello, Prévost (CA)

(73) Assignee: Orthosoft ULC, Montreal (CA)

( * ) Notice: Subject to any disclaimer, the term of this patent is extended or adjusted under 35 U.S.C. 154(b) by 119 days.

(21) Appl. No.: 17/552,492

(22) Filed: Dec. 16, 2021

(65) Prior Publication Data

US 2022/0183701 A1 Jun. 16, 2022

Related U.S. Application Data

(60) Provisional application No. 63/126,395, filed on Dec. 16, 2020.

(51) Int. Cl.
*A61B 17/02* (2006.01)
*A61B 17/16* (2006.01)
(Continued)

(52) U.S. Cl.
CPC .......... *A61B 17/1675* (2013.01); *A61B 34/20* (2016.02); *A61B 34/30* (2016.02); *A61B 2034/2055* (2016.02)

(58) Field of Classification Search
CPC .............. A61B 17/154; A61B 17/1675; A61B 2034/2055; A61B 2034/2068;
(Continued)

(56) References Cited

U.S. PATENT DOCUMENTS 8,038,683 B2   10/2011   Couture et al.
8,211,041 B2    7/2012   Fisher et al.
(Continued)

FOREIGN PATENT DOCUMENTS

CA         3142761 C        7/2024
WO   WO-2019226824 A1 *   11/2019    ............. A61B 34/10

OTHER PUBLICATIONS

"Canadian Application Serial No. 3,142,761, Office Action mailed Mar. 30, 2023", 5 pgs.
(Continued)

*Primary Examiner* — Samuel S Hanna
(74) *Attorney, Agent, or Firm* — SCHWEGMAN LUNDBERG & WOESSNER, P.A.

(57) ABSTRACT

To address technical problems facing knee arthroplasty resection validation, the present subject matter provides a tracked knee arthroplasty instrument for objective measurement of resection depth. By performing a precise comparison between the location of the tracked knee arthroplasty instrument and a reference location, the knee arthroplasty instrument measures and validates each tibial and femoral resection. To address technical problems facing validation of joint laxity following knee arthroplasty, the tracked knee arthroplasty instrument is shaped to validate the flexion gap and extension gap. When the tracked knee arthroplasty instrument is inserted between the resected tibial plateau and femoral head, the instrument shape validates whether the desired flexion gap and extension gap have been achieved.

10 Claims, 14 Drawing Sheets

(51) Int. Cl.
*A61B 34/20* (2016.01)
*A61B 34/30* (2016.01)

(58) Field of Classification Search
CPC . A61B 2090/3983; A61B 34/20; A61B 34/30; A61B 34/25
See application file for complete search history.

(56) References Cited

U.S. PATENT DOCUMENTS

| | | |
|---|---|---|
| 2005/0251148 A1 | 11/2005 | Friedrich et al. |
| 2006/0036257 A1* | 2/2006 | Steffensmeier ...... A61B 17/155 606/90 |
| 2019/0240045 A1 | 8/2019 | Couture |
| 2021/0137613 A1* | 5/2021 | Chi ........................ A61B 90/10 |
| 2021/0186614 A1* | 6/2021 | Forstein ................. G16H 20/40 |
| 2022/0370157 A1 | 11/2022 | Malon et al. |

OTHER PUBLICATIONS

"Canadian Application Serial No. 3,142,761, Response filed Jul. 31, 2023 to Office Action mailed Mar. 30, 2023", 23 pgs.
"European Application Serial No. 21215218.5, Extended European Search Report mailed May 16, 2022", 11 pgs.
"European Application Serial No. 21215218.5, Response filed Dec. 22, 2022 to Extended European Search Report mailed May 16, 2022", 25 pgs.
"European Application Serial No. 21215218.5, Invitation pursuant to Article 94(3) and Rule 71(1) EPC mailed Jul. 29, 2024", 6 pgs.

* cited by examiner

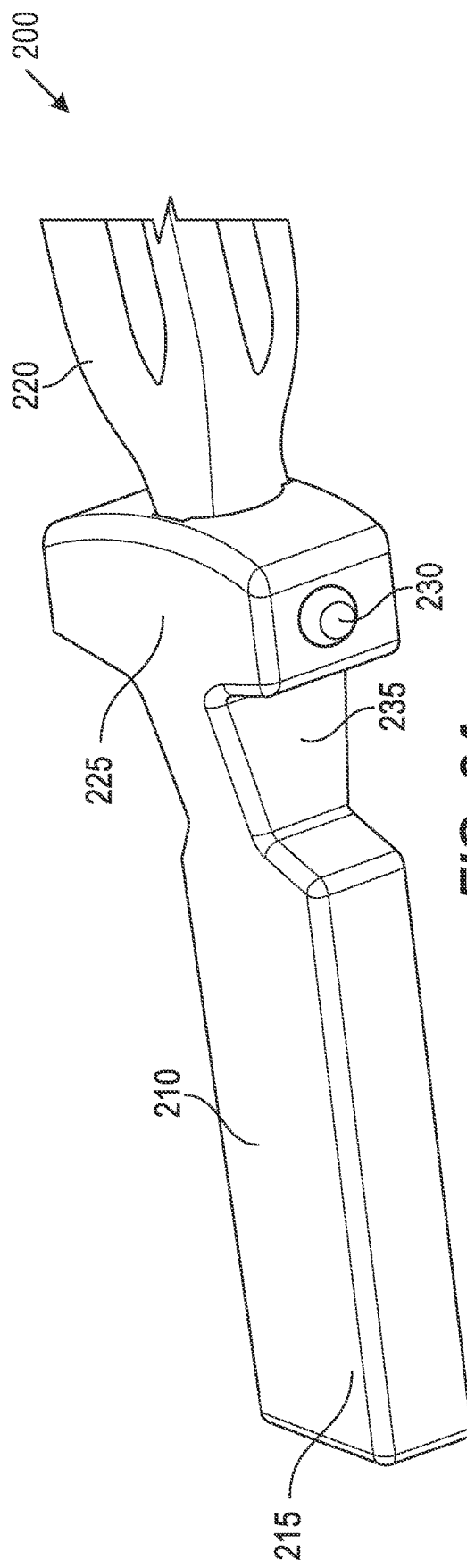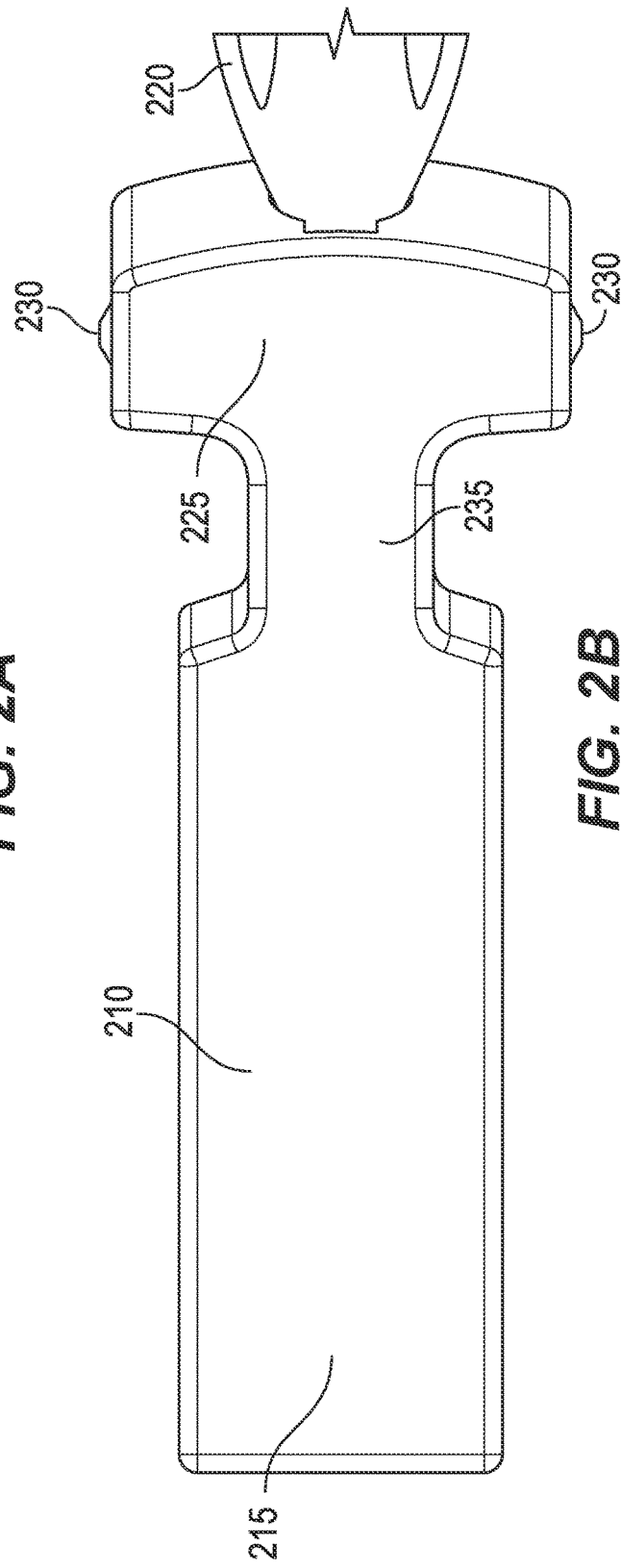
FIG. 2A
FIG. 2B

KNEE ARTHROPLASTY VALIDATION AND GAP BALANCING INSTRUMENTATION

CROSS-REFERENCE TO RELATED APPLICATION

This application is a continuation application of U.S. Provisional Patent Application No. 63/126,395, filed on Dec. 16, 2020, and entitled "Knee Arthroplasty Validation and Gap Balancing Instrumentation," the application of which is hereby incorporated by reference in its entirety.

FIELD

The present application relates to surgical knee replacement.

BACKGROUND

A knee replacement procedure (e.g., knee arthroplasty) is used to repair or replace damaged bone or damaged tissue in a patient knee joint. A knee arthroplasty includes repairing or replacing damaged or diseased articular surfaces of the tibia or femur. The arthroplasty procedure may include cutting (e.g., resecting) one or more articular surfaces of the tibia and femur and replacing a portion of each articular surface with a prosthesis (e.g., articular surface implant). A total knee arthroplasty (TKA) may be used to repair all articular surfaces of the tibia and femur, whereas a partial knee arthroplasty (PKA) may be used to repair a portion of the articular surfaces of the knee, such as the medial, lateral, or patellofemoral compartment. The TKA and PKA procedures require precise resections of the tibia and femur. The cut depth for each resection is specific to the patient and each prosthesis. A surgeon may validate a resection depth manually by inserting a trial prosthesis and exercising the knee through various motions. However, this resection validation is subjective and subject to errors. What is needed is an improved knee arthroplasty resection validation.

BRIEF DESCRIPTION OF THE DRAWINGS

FIGS. 2A-2B are perspective views of a tracked knee arthroplasty system, in accordance with some embodiments.

DETAILED DESCRIPTION

Figure 1:
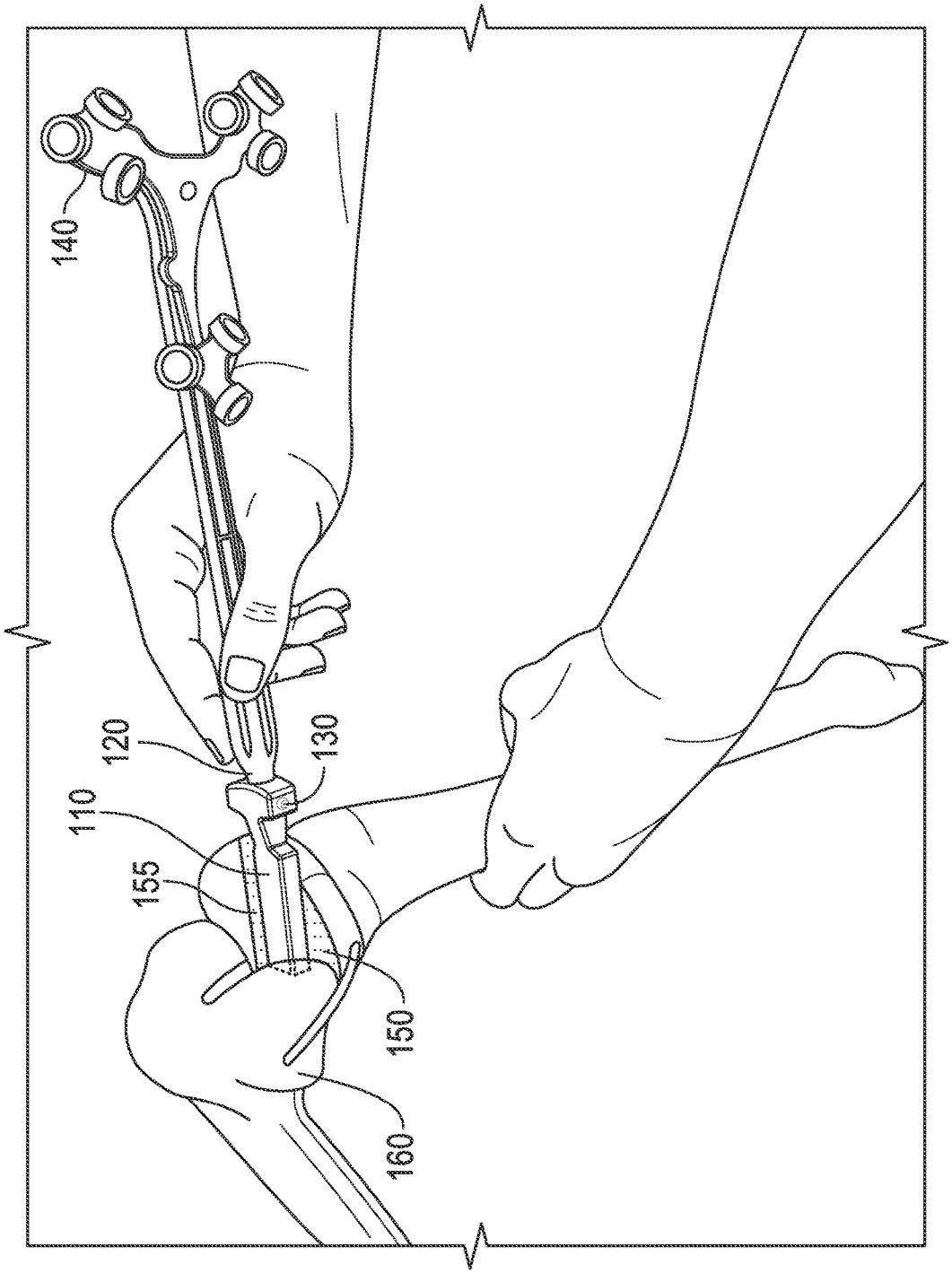
FIG. 1 is a perspective view of a tracked knee arthroplasty system, in accordance with some embodiments.

The present disclosure describes technical solutions to various technical problems facing knee arthroplasty procedures. To address technical problems facing knee arthroplasty resection validation, the present subject matter provides a tracked knee arthroplasty instrument for objective measurement of resection depth. By performing a precise comparison between the location of the tracked knee arthroplasty instrument and a reference location, the knee arthroplasty instrument measures and validates each tibial and femoral resection. To address technical problems facing validation of joint laxity following knee arthroplasty, the tracked knee arthroplasty instrument is shaped to validate the flexion gap and extension gap. When the tracked knee arthroplasty instrument is inserted between the resected tibial plateau and femoral head, the instrument shape validates whether the desired flexion gap and extension gap have been achieved.

In an example PKA surgical procedure, a tibia is resected, the tracked knee arthroplasty instrument is used to validate the resection and check flexion gap and extension gap, the femur is resected, and the tracked knee arthroplasty instrument is again used to validate the resection and check gaps. The use of the tracked knee arthroplasty instrument to validate resections and check gaps ensures that bone gaps and soil tissue allow for sufficient space for an implant and sufficient space in the postoperative elongated leg. In addition to validating resections and checking gaps, the use of the tracked knee arthroplasty instrument provides information regarding limb alignment and tactile feel of the resected surfaces.

The tracked knee arthroplasty instrument may be used with a robotic surgical device. In an example, a robotic surgical device may perform a tibial or femoral resection, and the tracked knee arthroplasty instrument may be used by a surgeon or by the robotic surgical device to validate resections and check gaps. In an example, the robotic surgical device may position resection surgical tools to prepare for the resection, a surgeon may perform a tibial or femoral resection, and the tracked knee arthroplasty instrument may be used by a surgeon or by the robotic surgical device to validate resections and check gaps. The robotic surgical system and tracked knee arthroplasty instrument may use a combination of one or more coordinate systems or tracked positioning systems. In an example, the tracked knee arthroplasty instrument is tracked using an optical tracking system, the robotic surgical device uses a robotic device coordinate system, and a surgical plan management system translates the tracked knee arthroplasty instrument position and robotic surgical device position into a common coordinate system viewable by the surgeon.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a perspective view of a tracked knee arthroplasty system 100, in accordance with some embodiments. System 100 includes an arthroplasty validation instrument 110, where instrument 110 includes one or more articular contact surfaces that may be placed in contact with a resected tibial surface. In an example, a horizontal resection validation surface on the bottom surface (not shown) of instrument 110 may be placed on the tibial plateau horizontal resection 150. Similarly, a vertical resection validation surface on the distant surface (not shown) of instrument 110 may be placed on the vertical resection 155 (e.g., tibial sagittal resection).

The thickness (e.g., height) of instrument 110 separates the top surface from the horizontal resection validation surface on the bottom surface (not shown) of instrument 110. This gap validation thickness may be used to validate the gap between the tibial plateau horizontal resection 150 and the femoral head 160. FIG. 1 shows the gap validation thickness being used to validate the extension gap while the knee is in flexion, though the gap validation thickness may also be used to validate the flexion gap while the knee is in extension.

Instrument 110 may be attached to a manual manipulation device 120. The manipulation device 120 may include grooves, a grip, or other surface to improve the ability of a surgeon to manipulate the instrument 110. The instrument 110 or the manipulation device 120 may include an orientation mechanism (e.g., detent, keying surface) to ensure the instrument 110 and manipulation device 120 are attached in a reliable and precise configuration. In an example, the instrument 110 includes a threaded aperture and the manipulation device 120 includes a threaded socket, and a threaded screw 130 is attached through the instrument 110 into the manipulation device 120.

The manipulation device 120 may be attached to a location tracking device 140, such as an optical tracker. The tracking device 140 may be used by an optical tracking system to determine the precise location of the instrument 110. In an example, once the instrument 110 is positioned against the horizontal resection 150 and against the vertical resection 155, the tracking device 140 may be used to validate the horizontal resection 150 and the vertical resection 155. The validation of the horizontal resection 150 may include determining a resection cut depth, a varus or valgus angle, a resection slope, or other horizontal resection geometry. The validation of the vertical resection 155 may include determining a resection rotation, a resection medial-lateral offset, or other vertical resection geometry.

In another example, the position of the instrument 110 may be tracked to ensure the instrument 110 is inserted to a sufficient depth between the tibial plateau horizontal resection 150 and the native femoral head 160 or a distal femoral resection, where the gap validation thickness (e.g., height) of instrument 110 is used to validate the gap between the tibial plateau horizontal resection 150 and the native femoral head 160 or a distal femoral resection. The optical system may determine the position of the tracking device 140 relative to another tracked position, such as relative to an optical tracker fixedly attached to the patient tibia, relative to a registration pointer attached to a robotic arm, or relative to another tracked position.

FIGS. 2A-2B are perspective views of a tracked knee arthroplasty system 200, in accordance with some embodiments. System 200 includes an arthroplasty validation instrument 210 attached to a manual manipulation device 220, such as using a threaded screw 130 threaded through instrument 210 into manipulation device 220. Instrument 210 may include a proximate portion 225 that is proximate to the manipulation device 220, and may include a distal portion 215 that is distal from the manipulation device 220.

As shown in FIG. 2A, the proximate portion 225 may be thicker than the distal portion 215. The use of different thicknesses may be used to validate different gap sizes, such as validating a posterior gap on a posterior portion of a tibial plateau resection and a larger anterior gap on an anterior portion of the tibial plateau resection. Instrument 210 may include a transition region 235 between the proximate portion 225 and the distal portion 215. The transition region 235 may facilitate insertion of the instrument 210 between the tibial plateau horizontal resection 150 and the femoral head 160, such as by providing a linear sigmoid, or other smooth transition between the proximate portion 225 and the distal portion 215.

As shown in FIG. 2B, the proximate portion 225 may be wider than the distal portion 215. The wider proximate portion 225 may be used to provide a mechanical stop, such as by providing a stop against an anterior tibial surface when inserted between the tibial plateau horizontal resection 150 and the femoral head 160.

Figure 3:
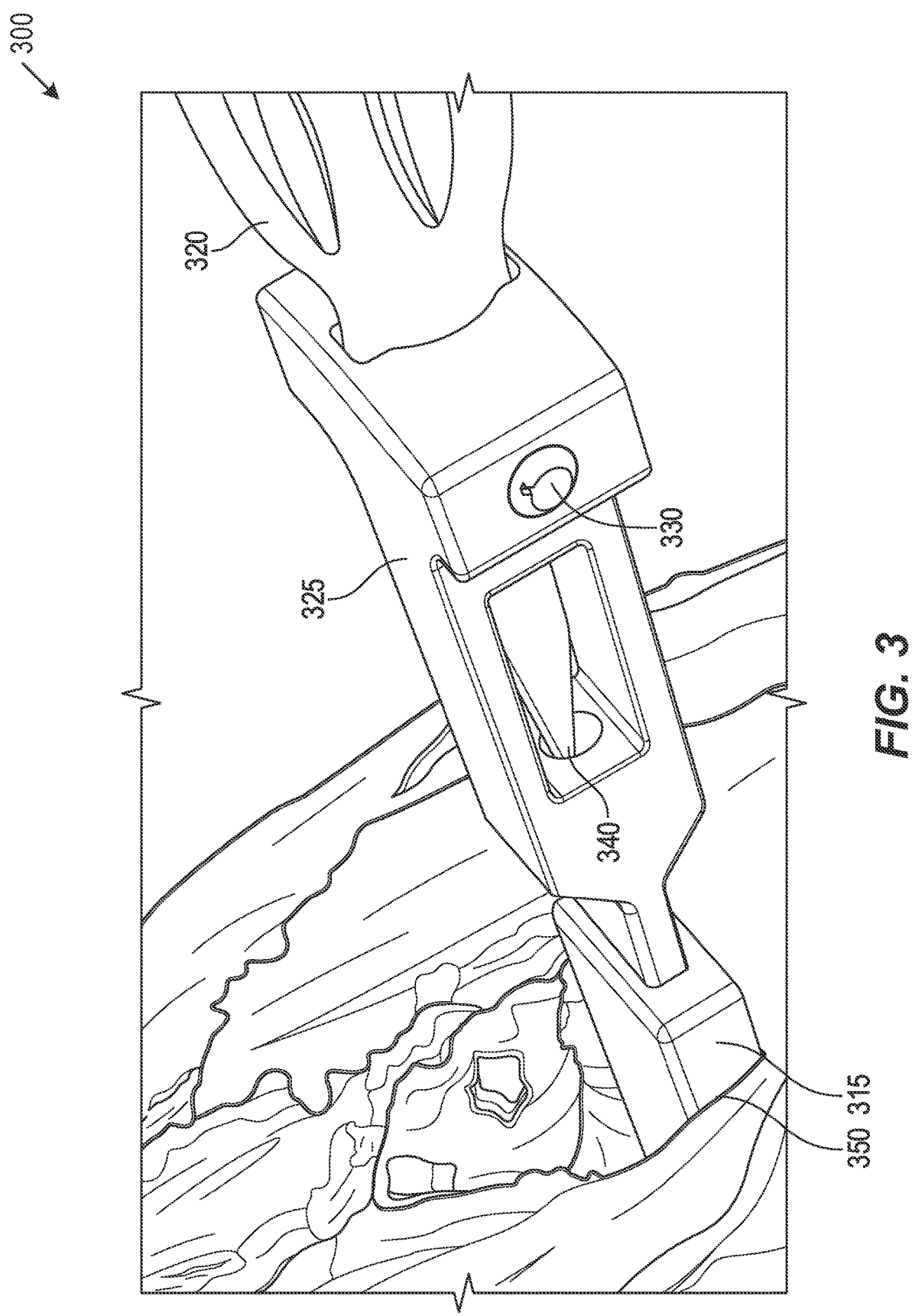
FIG. 3 is a perspective view of a tracked knee arthroplasty system, in accordance with some embodiments.

FIG. 3 is a perspective view of a tracked knee arthroplasty system 300, in accordance with some embodiments, System 300 includes a proximate portion 325 of an arthroplasty validation instrument, which may be inserted into a patient incision 350. The proximate portion 325 may be attached to a manual manipulation device 220. The manipulation device 320 may include a pointed tip portion 340 that is received within a tip receptacle within proximate portion 325. Once the pointed tip portion 340 is seated correctly within the tip receptacle, the manipulation device 320 may be secured to the proximate portion 325 using a threaded screw 330.

Figure 4:
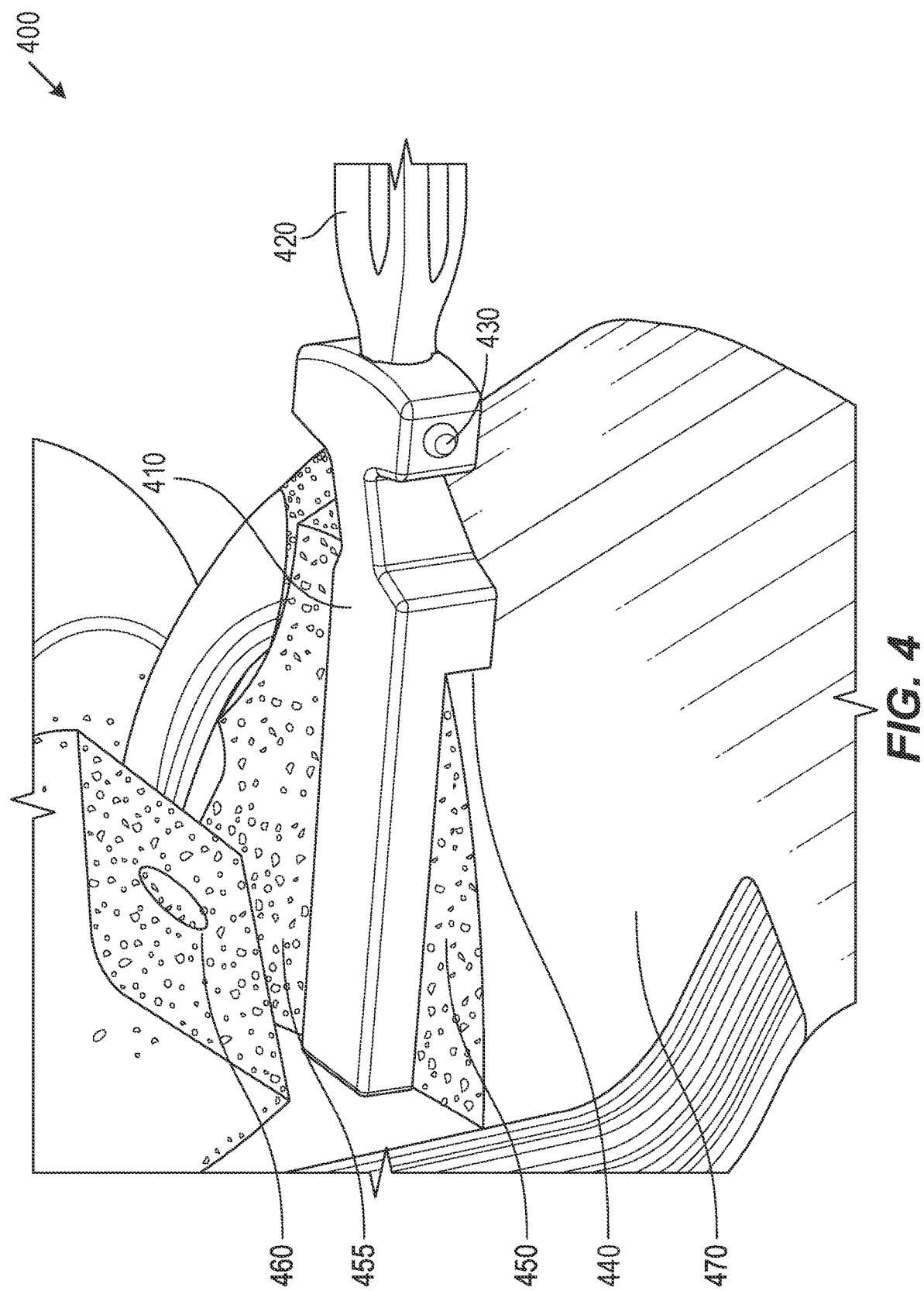
FIG. 4 is a perspective view of a tracked knee arthroplasty system, in accordance with some embodiments.

FIG. 4 is a perspective view of a tracked knee arthroplasty system 400, in accordance with some embodiments. System 400 includes an arthroplasty validation instrument 410, where instrument 410 includes one or more articular contact surfaces that may be placed in contact with a resected tibial surface. A horizontal resection validation surface on the bottom surface (not shown) of instrument 410 may be placed on the tibial plateau horizontal resection 450. Similarly, a vertical resection validation surface on the distant surface (not shown) of instrument 410 may be placed on the vertical resection 455 (e.g., tibial sagittal resection). Instrument 410 may be attached to a manual manipulation device 420, such as using a threaded screw 430 threaded through instrument 410 into the manipulation device 420, Manipulation device 420 may be connected to an optical tracker or other tracking device (not shown).

The thickness of instrument 410 separates the top surface from the horizontal resection validation surface on the bottom surface (not shown) of instrument 410. This gap validation thickness may be used to validate the gap between the tibial plateau horizontal resection 450 and the resected femoral head 460. FIG. 4 shows the gap validation thickness being used to validate the extension gap while the knee is in flexion, though the gap validation thickness may also be used to validate the flexion gap while the knee is in extension.

Instrument 410 includes an anterior stop 440. When fully inserted, the anterior stop 440 rests against the tibial anterior cortex 470. The anterior stop 440 may be used to minimize or prevent instrument 410 from migrating during drilling, pinning, impaction, or other surgical procedures. When used with a tracking device, the anterior stop 440 may be used to provide key cortex location information or other tracking information, which may be used to make more precise recuts in imageless cases. This tracking information may reduce or prevent the need for discrete (e.g., dedicated) digitization or registration pointer checks.

Instrument 410 may include one or more structural features to provide additional validation information. The length of instrument 410 may be used to locate the tibial posterior cortex while validating the tibial plateau resection plane. In an example, instrument 410 may include distal tibial hooks, distal tibial stops, or other mechanical features (not shown) extending beyond the end of instrument 410 to locate the posterior cortex. This determined location of the posterior cortex may assist in finding additional reference locations for anatomic landmarking, such as to define the tibial internal and external rotation coordinate system at the plane of the tibial resection. The combination of distal tibial hook and the anterior stop 440 may be used to provide information about the geometry of the tibia, which may be used to size the tibia. In an example, instrument 410 may include medial or lateral tibial side hooks or other mechanical features (not shown) extending to either side of instrument 410. The side hooks may be used to map the size and geometry of the medial cortex or lateral cortex. This cortex information may be used for femoral sizing, such as selecting standard or narrow femoral head implants. In an example, instrument 410 may include a distal trochlea stylus (not shown), which might be used to locate or map the femoral trochlea (e.g., intercondylar fossa of femur). The trochlea stylus may provide anterior reference information, which may be used to improve femoral sizing or notching information within a resection. Information from the anterior stop 440 or one or more tibial hooks may be used to validate resections or update anatomic information. In an example, anatomic information may be gathered through preoperative digitization of the bone, and the preoperatively gathered information may be updated using intraoperative information gathered from the anterior stop 440 or one or more tibial hooks. This updated information may be used to refresh or improve surgical plans intraoperatively while reducing or minimizing additional intraoperative surgical procedure steps.

Figure 5:
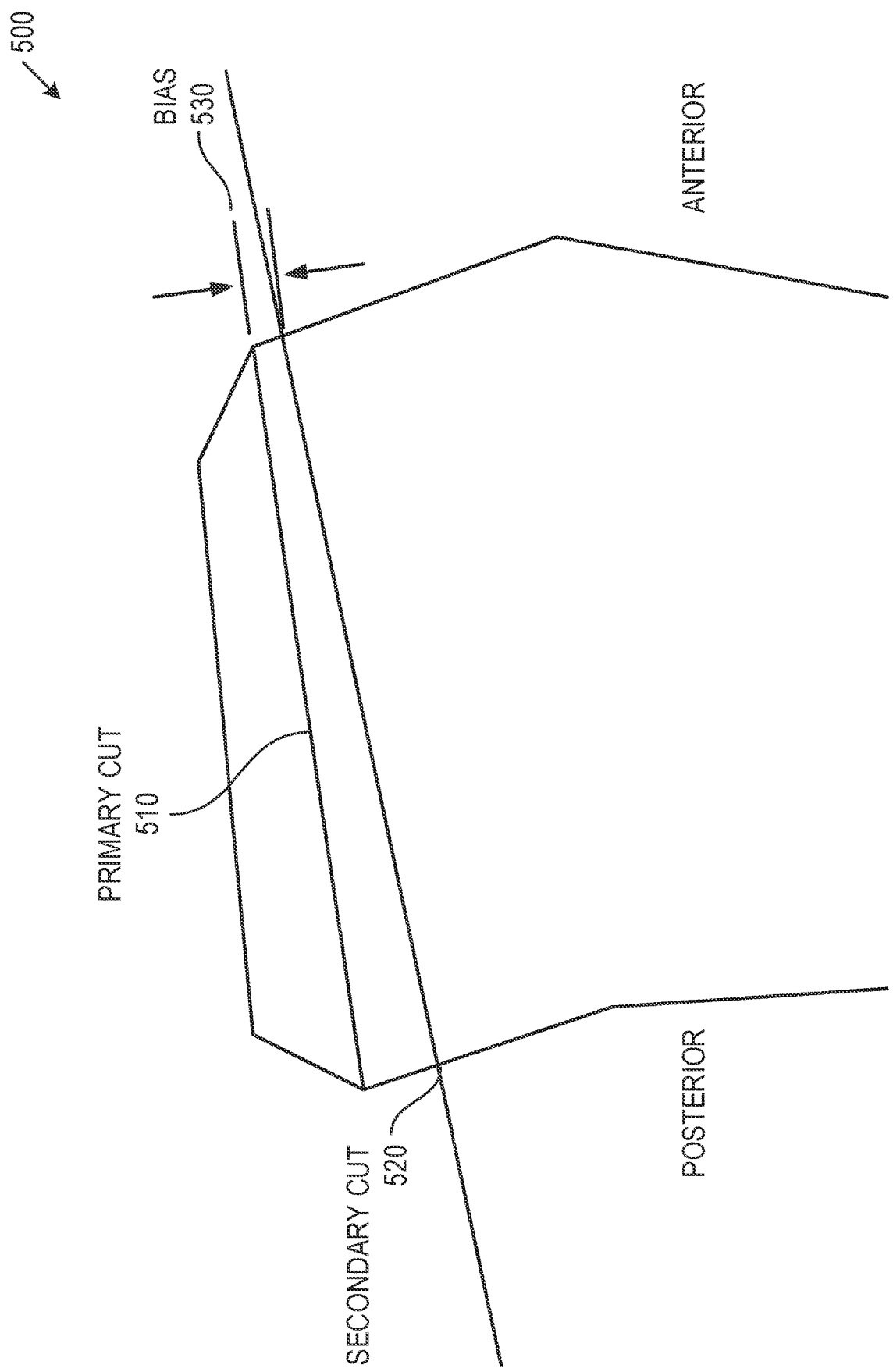
FIG. 5 is a tibial resection diagram, in accordance with some embodiments.

FIG. 5 is a tibial resection diagram 500, in accordance with some embodiments. A surgeon may use an arthroplasty validation instrument to determine that the depth or slope of the primary cut 510 (e.g., initial tibial resection) is insufficient, and that a secondary cut 520 (e.g., secondary resection) may be needed. To change the slope of a tibial resection, the secondary cut 520 must begin at a lower point on the tibial anterior cortex to ensure a full resection. The starting points of the primary cut 510 and the secondary cut 520 may be separated by a cut bias 530. To minimize the number of additional tibial resections, the cut bias 530 may be selected to be the smallest bias that is sufficiently large to perform the secondary cut 520. This may be particularly useful when performing a secondary cut 520 where there is insufficient information available about the location of the tibial anterior cortex, such as in imageless arthroplasty procedures. The bias selection may be improved by determining information about the location of the anterior cortex, such as using the anterior stop 440 to provide cortex location information.

Figure 6:
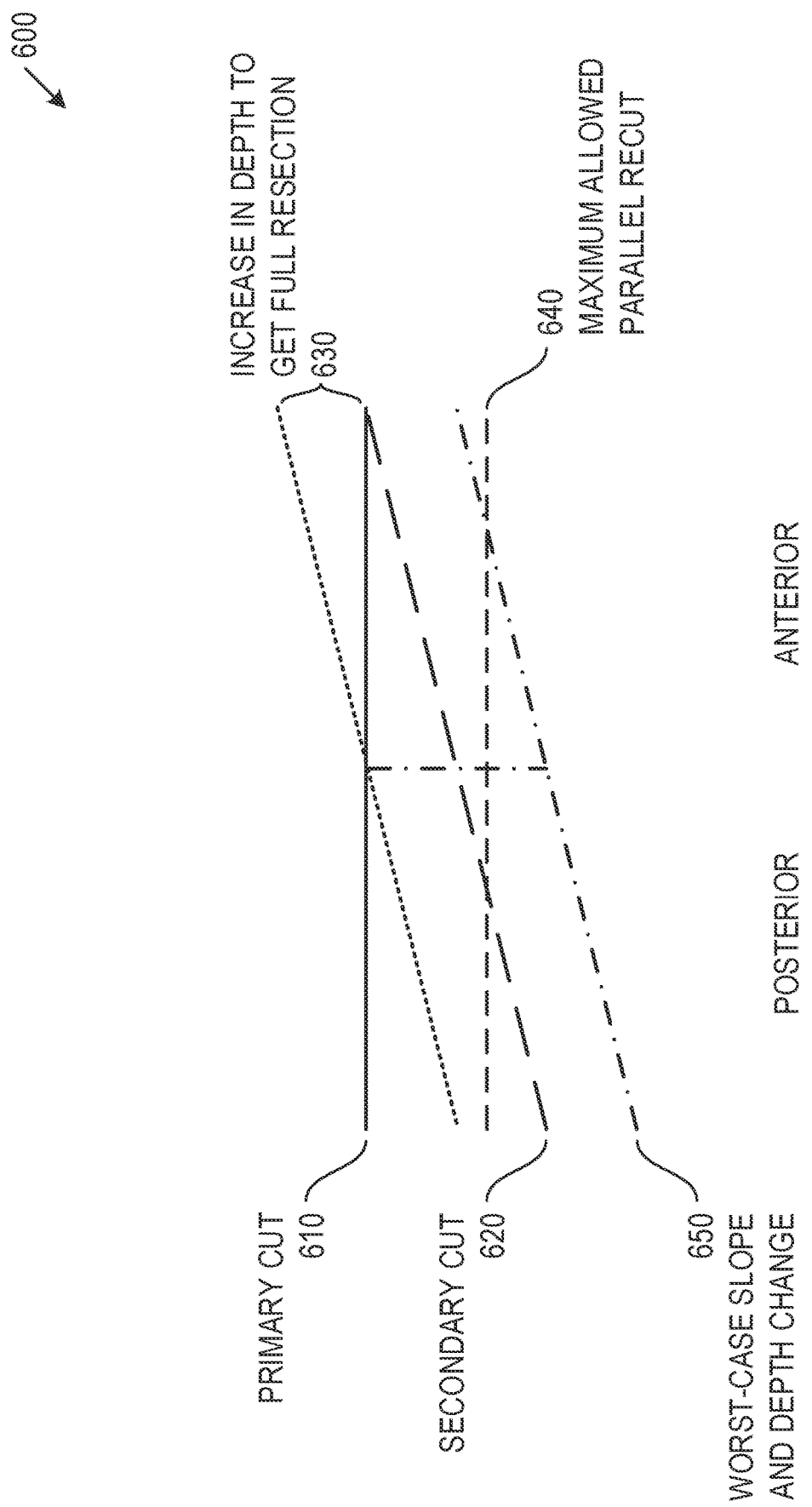
FIG. 6 is a tibial resection slope graph, in accordance with some embodiments.

FIG. 6 is a tibial resection slope graph 600, in accordance with some embodiments. Graph 600 depicts an example primary cut 610 and a secondary cut 620. In a conventional TKA surgery, the rotation point for the posterior slope is set at the anterior aspect of the tibia, so, the surgeon does not need to worry about increased resection depth for an increased slope recut. For a PKA surgery, the posterior slope is set based on the middle of the tibial plateau, so a secondary cut to change the slope will always include an increase in the resection depth 630 (e.g., secondary cut bias) to ensure a full resection.

The slope and depth of the secondary cut 620 may be adjustable to provide a desired slope while remaining consistent with other surgical parameters. In an example, a PKA surgical plan may have an associated maximum allowed parallel recut 640, which may correspond with a worst-case slope and depth change 650. Table 1 shows various combinations of tibial resection depth and slope. In particular, Table 1 shows a minimum increase in depth required to provide a full resection, and shows the maximum increase in resection depth that will result in a resection within 3 mm distal to the primary cut on the anterior/posterior side (e.g., maximum allowed parallel recut).

TABLE 1

Tibial Resection Depth and Slope

| Change in Slope (with respect to first cut) | Minimum change in resection depth | Minimum change in resection depth required for full resection | Maximum increase in resection depth (for minimum resection depth change) |
| --- | --- | --- | --- |
| 0° | 0.0 | 0 mm | 3 mm |
| 2° | 0.72 | 1.1 mm | 3.7 mm |
| 4° | 1.43 | 2.17 mm | 4.4 mm |
| 5° | 1.79 | 2.71 mm | 4.8 mm |
| 6° | 2.15 | 3.26 mm | 5.1 mm |
| 8° | 2.88 | 4.36 mm | 5.9 mm |
| 10° | 3.61 | 5.5 mm | 6.6 mm |

Figure 7:
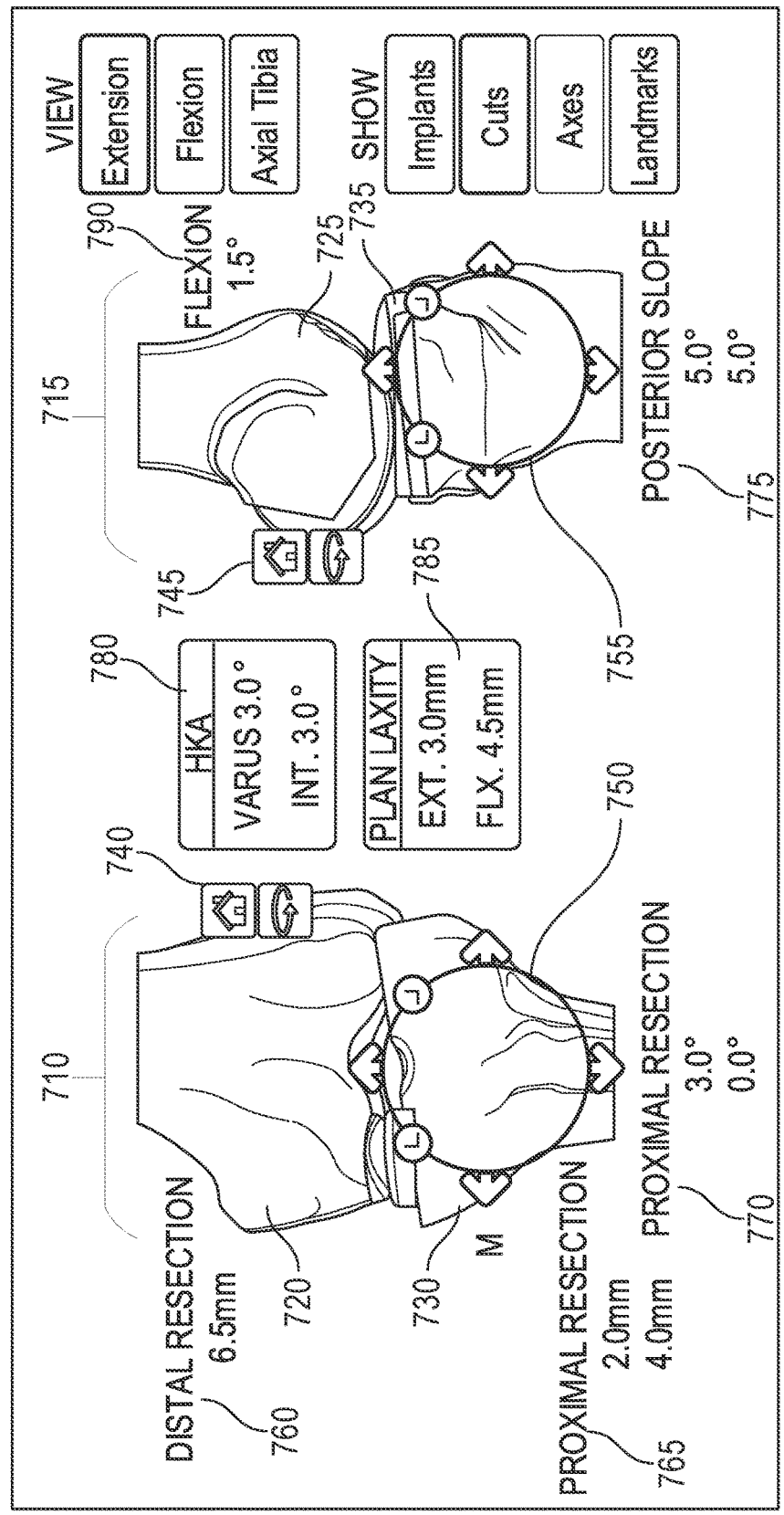
FIG. 7 is a diagram of a knee arthroplasty graphical user interface (GUI), in accordance with some embodiments.

FIG. 7 is a diagram of a knee arthroplasty graphical user interface (GUI) 700, in accordance with some embodiments. GUI 700 may be used to display information about planned or measured arthroplasty resection depths or angles. GUI 700 may include an anterior view 710 of the femoral head 720 and the proximal tibia 730. Similarly, GUI 700 may include a medial view 715 of the femoral head 725 and the proximal tibia 735. The anterior view 710 may have an associated anterior view control 740, and the medial view 715 may have an associated medial view control 745, which may be used to rotate the view of the femur and tibia displayed within GUI 700. The anterior view 710 may have an associated anterior tibial control 750, and the medial view 715 may have an associated medial tibial control 755, which may be used to change the flexion angle or modify tibial slope or resection. GUI 700 may also provide information about distal resection depth 760, proximal resection depth 765, proximal resection slope angles 770, posterior slope angles 775, hip-knee-ankle (HKA) axis angles 780, plan laxity measurements 785, and a flexion angle 790.

The display of information, bone views, or other portions within GUI 700 may be modified to indicate whether one or more steps in the knee arthroplasty surgical procedure have been completed. For example, the proximal resection depth 765 may be presented in a first color to indicate a sufficient resection depth, and the proximal tibia 730 and proximal resection angle 770 may be presented in a second color to indicate additional surgical procedure steps are needed to provide the planned resection slope. In another example, the proximal resection depth 765 may be presented in a first color to indicate the depth is based on a depth validated by an arthroplasty validation instrument, and the proximal tibia 730 and proximal resection angle 770 may be presented in a second color to indicate the displayed resection slope angle is using outdated information.

Figure 8A:
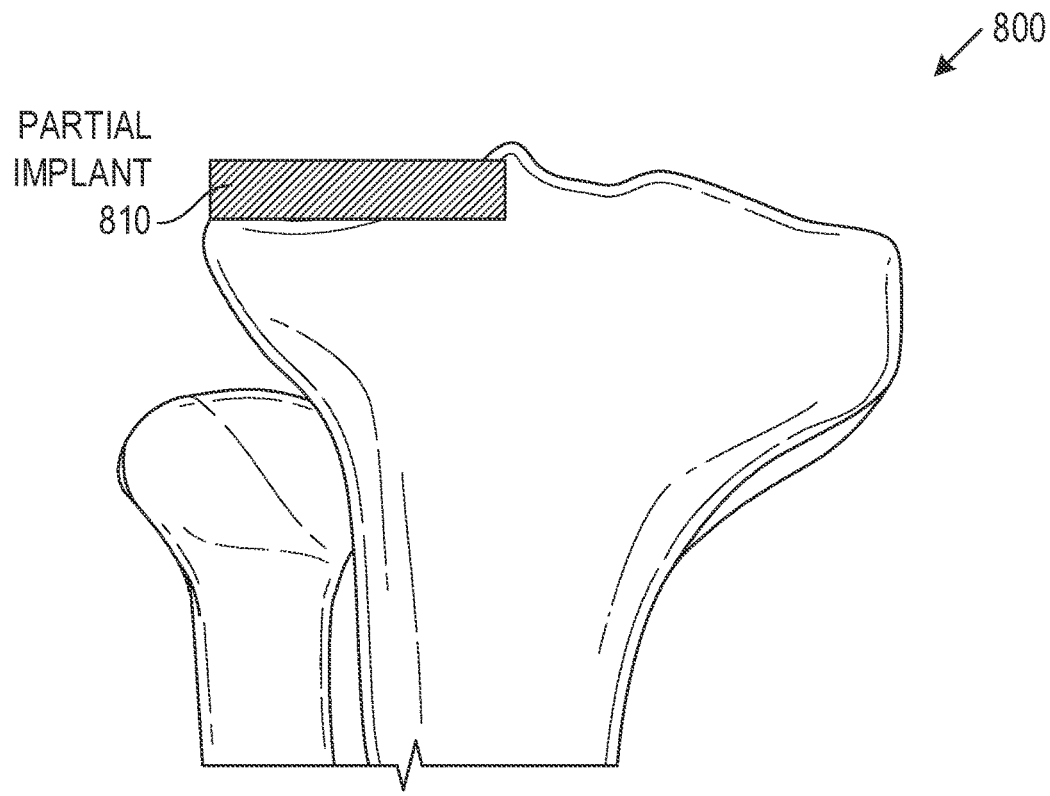
FIGS. 8A-8D are diagrams of an augment cut validation, in accordance with some embodiments.
Figure 8B:
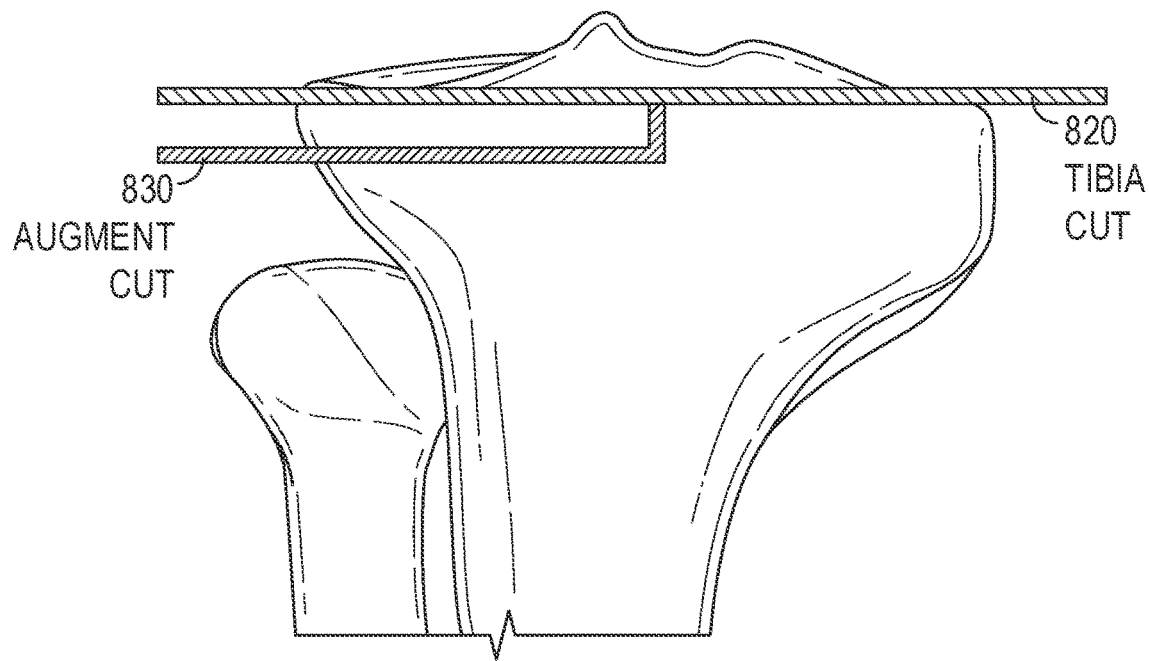
Figure 8C:
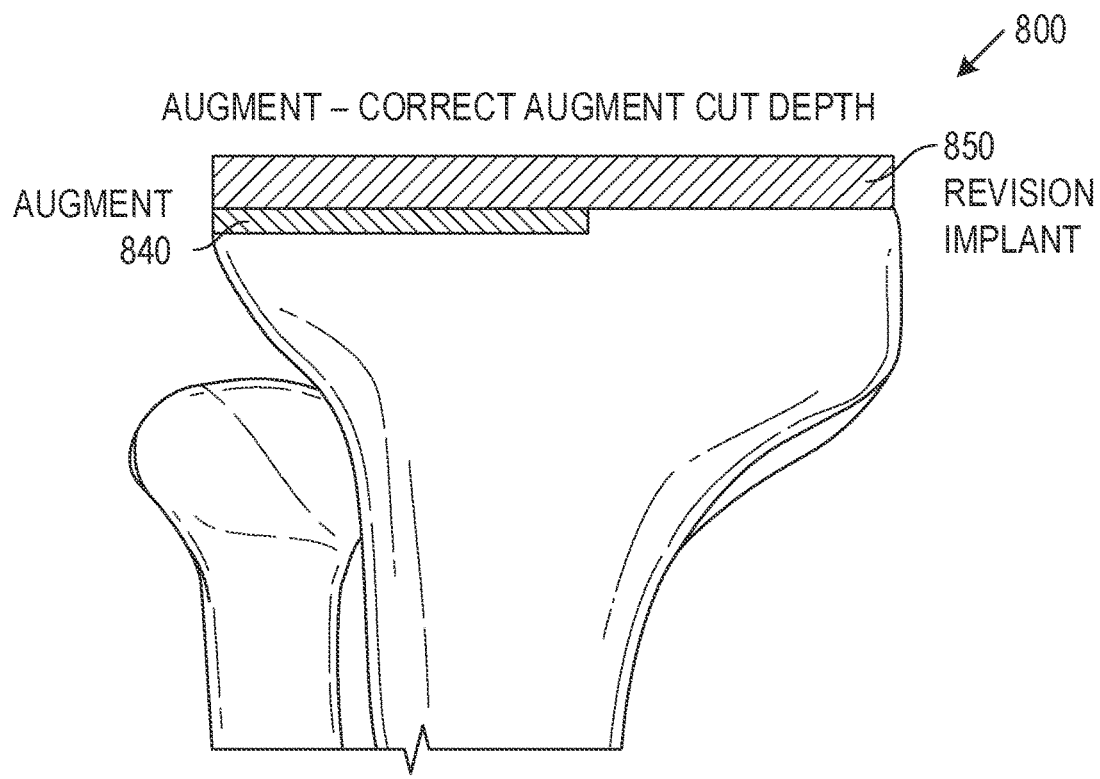
Figure 8D:
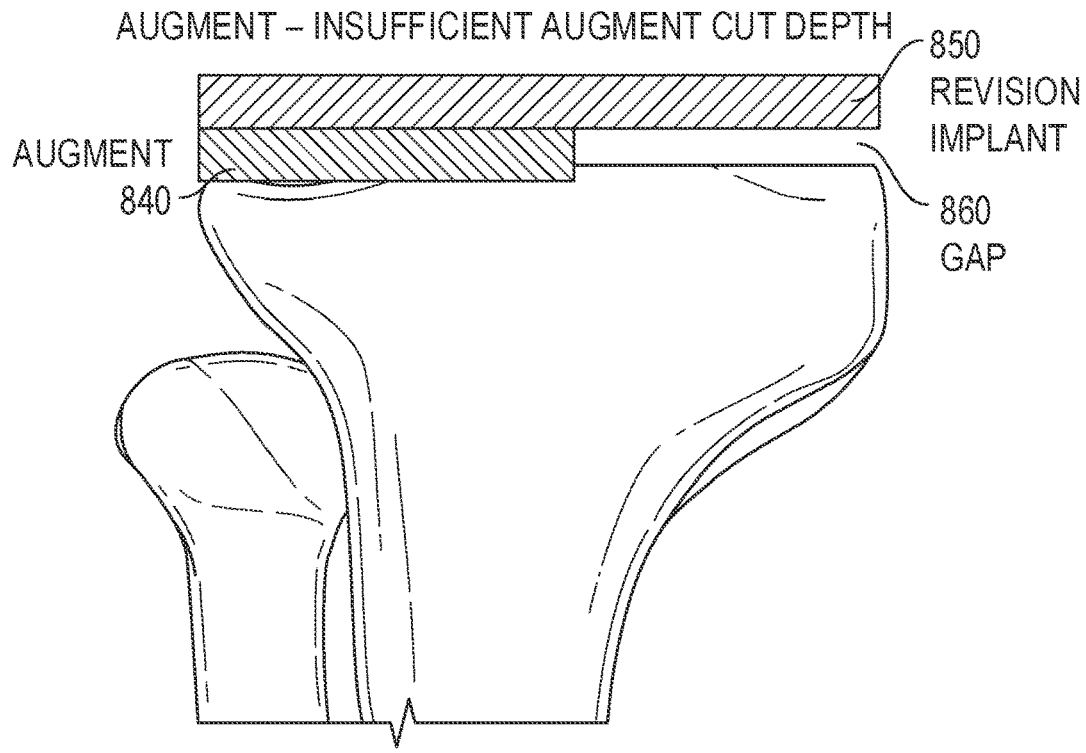

FIGS. 8A-8D are diagrams of an augment cut validation 800, in accordance with some embodiments. FIG. 8A shows a patient tibia with a partial implant 810, such as may be used in a PKA surgical procedure. FIG. 8B shows a horizontal revision surgery tibia cut 820 and a deeper augment cut 830. A surgeon may use the revision surgery when a portion of the knee has bad bone quality, where the surgeon can remove the bad bone quality region with an augment implant to provide a stable surface for the femoral implant. FIG. 8C shows the revision surgery with an augment implant 840 and a revision implant 850. While FIG. 8C shows a revision surgery with a correct augment implant cut depth, FIG. 8D shows a revision surgery with an insufficient augment implant cut depth, resulting in a gap 860. To determine whether the augment implant cut depth is sufficient, an augment cut validation device may be used, such as shown in FIG. 9A.

Figure 9A:
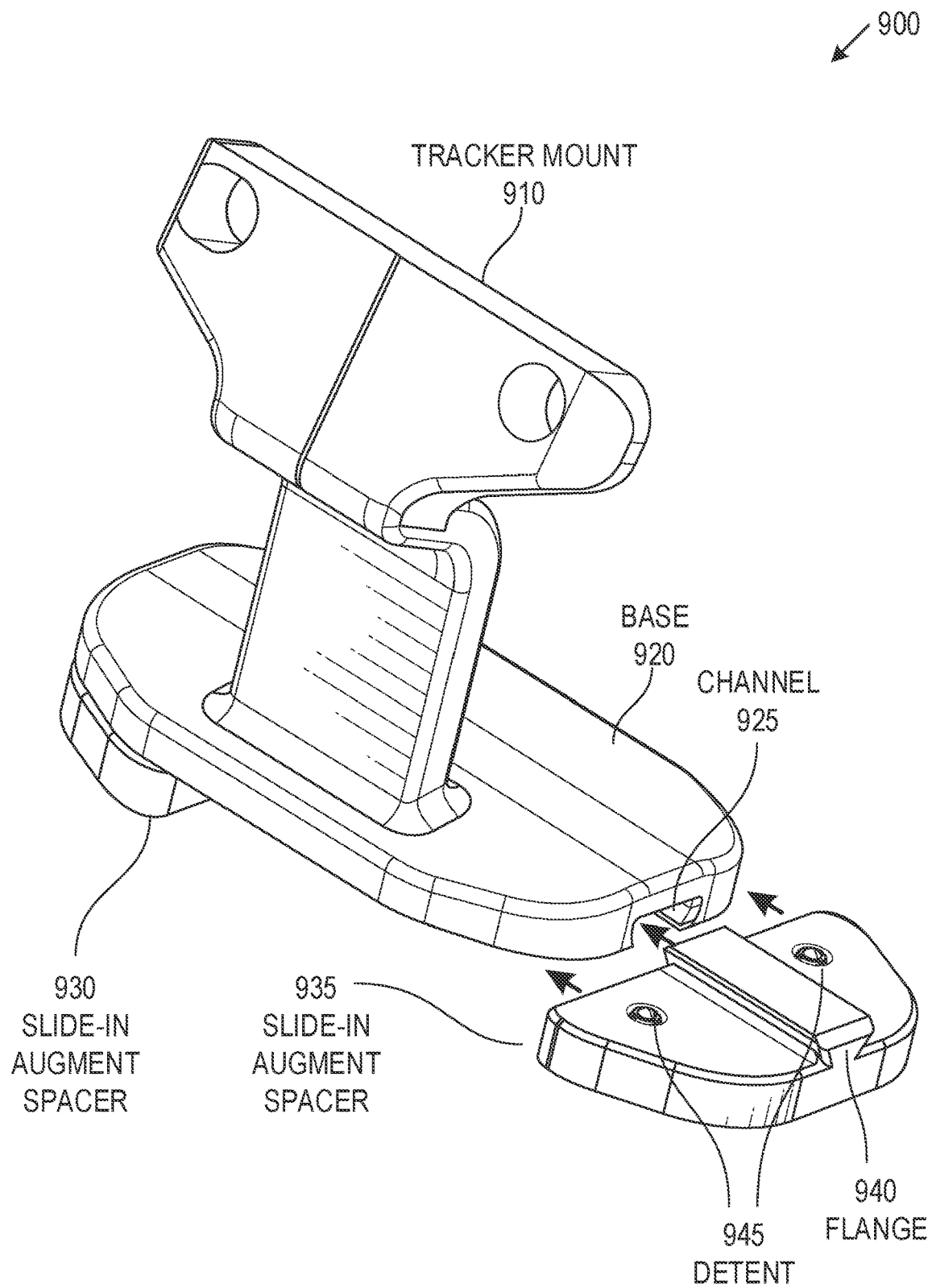
FIGS. 9A-9C are diagrams of an augment cut validation device, in accordance with some embodiments.
Figure 9B:
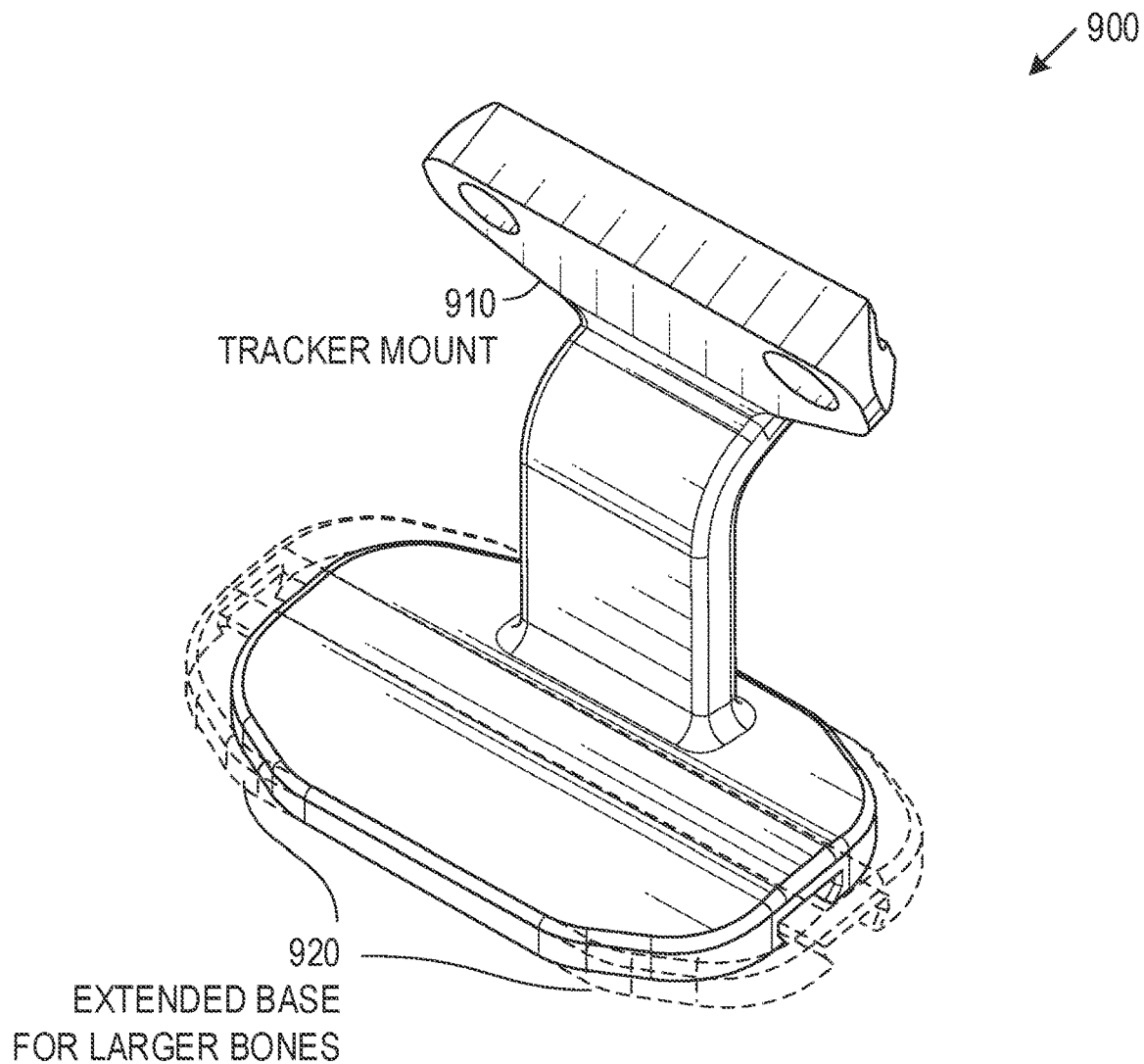
Figure 9C:
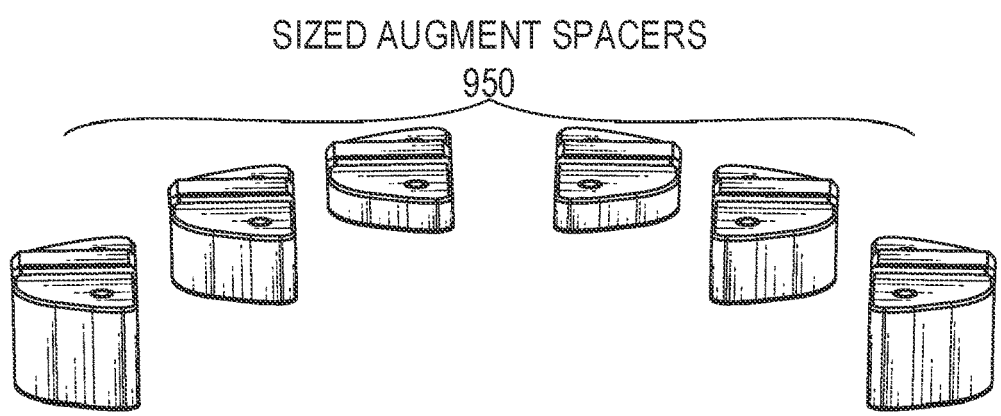

FIGS. 9A-9C are diagrams of an augment cut validation device 900, in accordance with some embodiments. The augment cut validation device 900 may be used to determine whether a revision surgery augment resection and horizontal resection are cut to a correct depth. As shown in FIG. 9A, augment cut validation device 900 may include a tracker mount 910 and a base 920. One or more slide-in augment spacers 930, 935 may be attached to base 920. In an example, each augment spacer 930, 935 may have a flange 940 that slides within base channel 925 and one or more detents 945 to secure the augment spacer 930, 935 in a fixed position relative to the augment cut validation device 900. As shown in FIG. 9B, an augment cut validation device 900 may have an extended base for validating a surface on a larger bone. As shown in FIG. 9C, variously sized augment spacers 950 may be used. In various examples, the augment spacers 950 may include incremental sizes, such as 5 mm, 10 mm, 15 mm, or other sizes. In an example, two different sized augment spacers 950 may be used to validate a first cut dept of a resected surface of a horizontal resection and a deeper cut depth of a resected surface of an augment resection.

Figure 10:
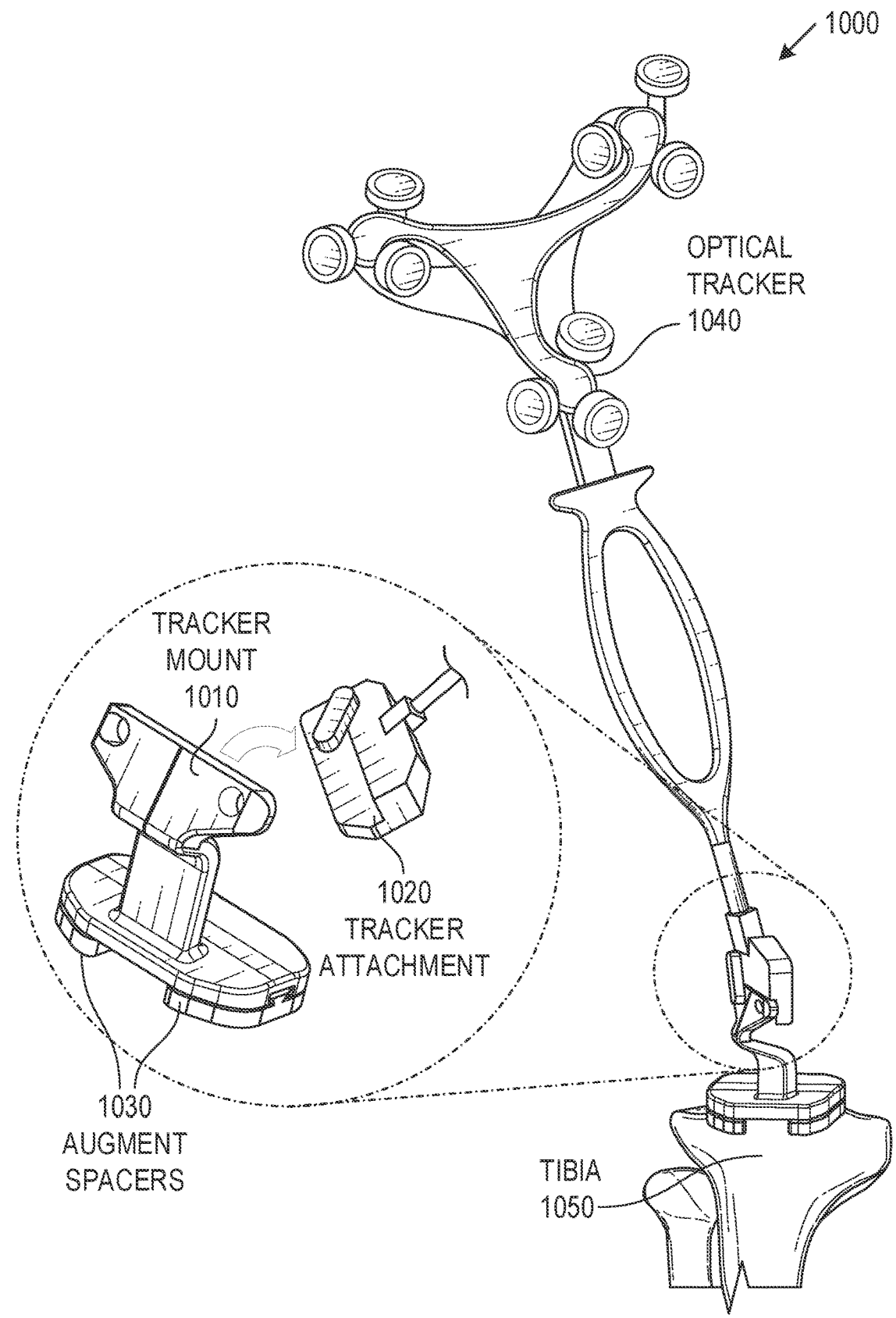
FIG. 10 is a diagram of an augment cut validation tracker device, in accordance with some embodiments.

FIG. 10 is a diagram of an augment cut validation tracker device 1000, in accordance with some embodiments. The augment cut validation tracker device 1000 includes a tracker mount 1010 that attaches to a tracker attachment 1020, which is fixedly attached to an optical tracker 1040. The augment cut validation tracker device 1000 includes one or more augment spacers 1030 that may be used to validate a revision surgery augment resection and horizontal resection. In an example, surgeon may position the augment cut validation tracker device 1000 such that the augment spacers 1030 are in contact with an augment resection and horizontal resection of a patient tibia 1050, and the optical tracker 1040 may be used to determine the depth of the augment resection and horizontal resection by comparing a measured location of the optical tracker 1040 against a known location of the tibia 1050. Similarly, the augment cut validation tracker device 1000 may be used to compare the augment resection depth to the horizontal resection depth, such as by determining that a vertical axis of the optical tracker 1040 is offset from the vertical axis of the tibia 1050.

Figure 11:
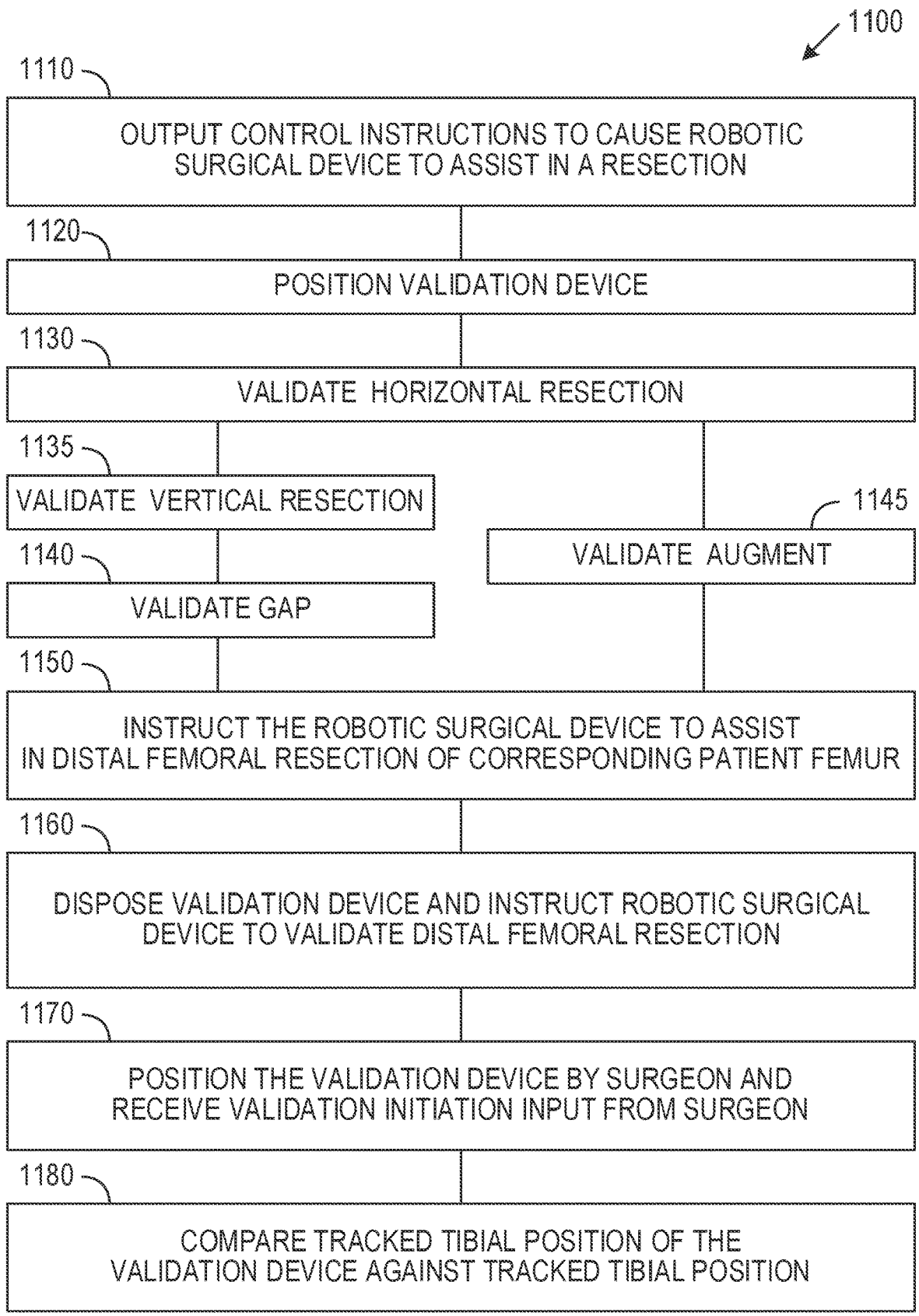
FIG. 11 illustrates a flow chart showing a knee arthroplasty technique, in accordance with some embodiments.

FIG. 11 illustrates a flow chart showing a knee arthroplasty technique 1100, in accordance with some embodiments. Technique 1100 may include outputting 1110 control instructions to cause a robotic surgical device to assist in a resection of a patient tibia or femur. The resection may include a tibial plateau resection, which may include a resected horizontal surface and a resected vertical surface. The resection may include an augment resection, which may include a resected augment surface and a resected revision implant surface.

Technique 1100 includes positioning 1120 a knee arthroplasty validation device to contact the horizontal resection and to contact the vertical resection. Positioning of the knee arthroplasty validation device may include outputting control instructions to cause the robotic surgical device to position the knee arthroplasty validation device. The knee arthroplasty validation device may include a horizontal resection validation surface, a vertical resection validation surface, one or more augment spacers, and an optical tracker fixedly attached to the knee arthroplasty validation device. The vertical resection validation surface may be orthogonal to the horizontal resection validation surface, and a substantially planar gap validation surface. The gap validation surface may be substantially parallel to the horizontal resection validation surface and separated from the horizontal resection validation surface by a gap validation thickness. The gap validation thickness may be used to validate a flexion gap and an extension gap.

Technique 1100 includes validating 1130, using processing circuitry of the robotic surgical device, the horizontal resection based on a tracked validation position of the optical tracker. Technique 1100 may include validating 1135, using processing circuitry of the robotic surgical device, the vertical resection based on a tracked validation position of the optical tracker. Technique 1100 may include validating 1145, using processing circuitry of the robotic surgical device, an augment resection based on a tracked validation position of the optical tracker.

Technique 1100 may include validating 1140 a flexion gap or an extension gap. Validating 1140 the flexion gap may include comparing the gap validation thickness of the knee arthroplasty validation device against the flexion gap formed by the patient tibia and a corresponding patient femur in flexion. Validating 1140 the extension gap may include comparing the gap validation thickness of the knee arthroplasty validation device against the extension gap formed by the patient tibia and the corresponding patient femur in extension.

Technique 1100 may include instructing 1150 the robotic surgical device to assist in a distal femoral resection of corresponding patient femur. Technique 1100 may include disposing 1160 the knee arthroplasty validation device against the distal femoral resection and instructing the robotic surgical device to validate the distal femoral resection based on a tracked femoral position of the knee arthroplasty validation device.

Technique 1100 may include a surgeon positioning 1170 the knee arthroplasty validation device and receiving a validation initiation input from the surgeon. The validation input may initiate the validation of the horizontal resection and the vertical resection.

Technique 1100 may include comparing 1180 the validation position of the knee arthroplasty validation device against a tracked tibial position. The tracked tibial position may be based on an optical tibial tracker fixedly attached to the patient tibia. The tracked tibial position may be based on a registration position of a registration pointer, where the registration pointer is fixedly attached to a robotic arm of the robotic surgical device.

Figure 12:
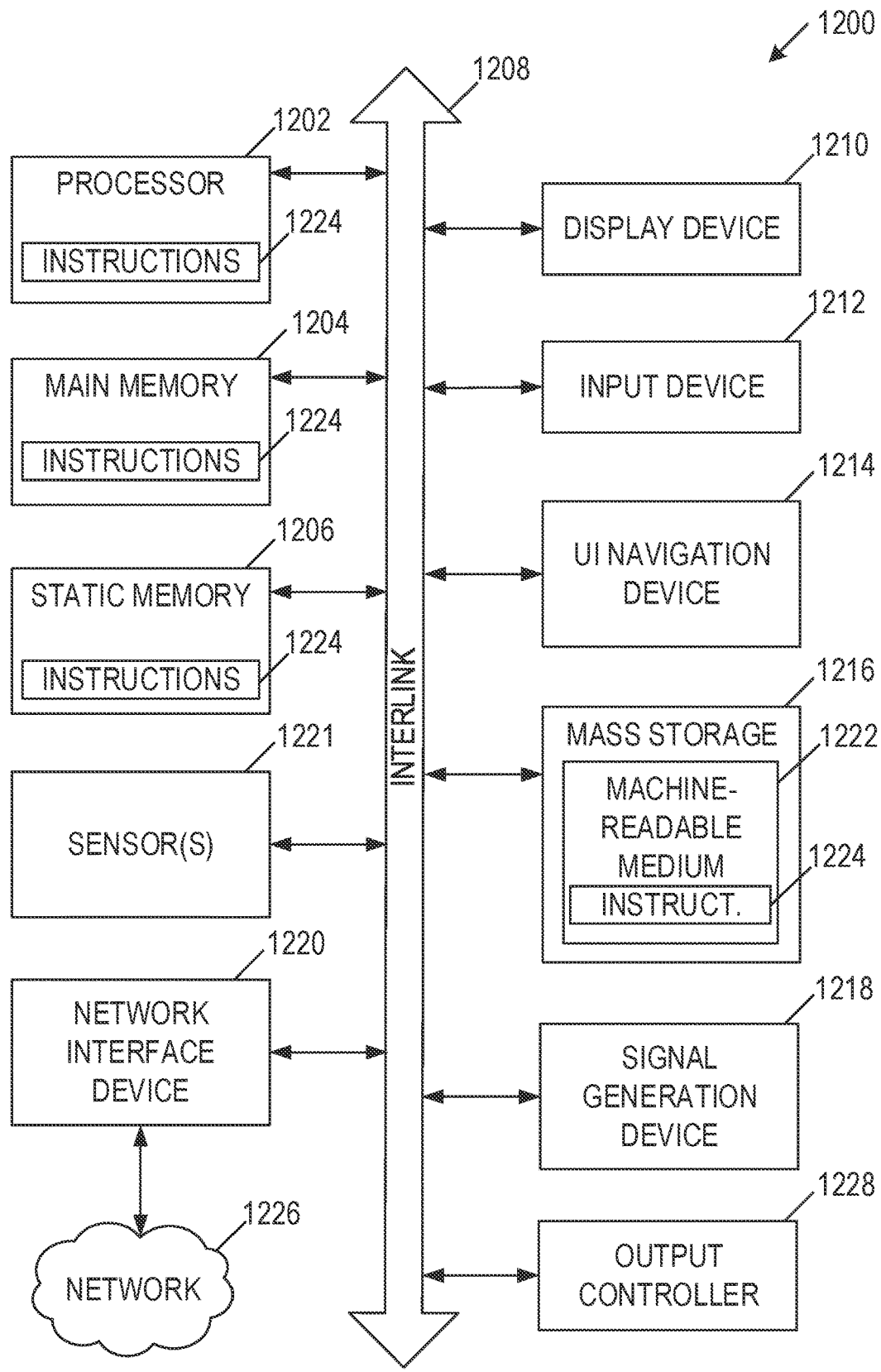
FIG. 12 illustrates an example of a block diagram of a machine upon which any one or more of the techniques (e.g., methodologies) discussed herein may perform in accordance with some embodiments.

FIG. 12 illustrates an example of a block diagram of a machine 1200 upon which any one or more of the techniques (e.g., methodologies) discussed herein may perform in accordance with some embodiments. In alternative embodiments, the machine 1200 may operate as a standalone device or may be connected (e.g., networked) to other machines. In a networked deployment, the machine 1200 may operate in the capacity of a server machine, a client machine, or both in server-client network environments. The machine 1200 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1200 may include a hardware processor 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210, an alphanumeric input device 1212 (e.g., a keyboard), and a user interface (IA) navigation device 1214 (e.g., a mouse). In an example, the display unit 1210, alphanumeric input device 1212 and UI navigation device 1214 may be a touch screen display. The display unit 1210 may include goggles, glasses, an augmented reality (AR) display, a virtual reality (VR) display, or another display component. For example, the display unit may be worn on a head of a user and may provide a heads-up-display to the user. The alphanumeric input device 1212 may include a virtual keyboard (e.g., a keyboard displayed virtually in a VR or AR setting.

The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensor. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices.

The storage device 1216 may include a machine readable medium 1222 that is non-transitory on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1200. In an example, one or any combination of the hardware processor 1202, the main memory 1204, the static memory 1206, or the storage device 1216 may constitute machine readable media.

While the machine readable medium 1222 is illustrated as a single medium, the term "machine readable medium" may include a single medium or multiple media (e.g., a centralized or distributed database, or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 may further be transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 1200, and includes digital or analog communications signals or other intangible medium to facilitate communication of such software.

Each of the following non-limiting examples may stand on its own, or may be combined in various permutations or combinations with one or more of the other examples:

Example 1 is a knee arthroplasty validation method for intraoperative validation of cut surfaces, the method comprising: outputting control instructions to cause a robotic surgical device to assist in a tibiofemoral joint resection of a patient tibia or a patient femur, the tibiofemoral joint resection including a horizontal resection; positioning a knee arthroplasty validation device to contact the horizontal resection, the knee arthroplasty validation device including a horizontal resection validation surface and an optical tracker fixedly attached to the knee arthroplasty validation device; validating, using processing circuitry of the robotic surgical device, the horizontal resection based on a tracked validation position of the optical tracker; and triggering an update of a display to indicate completion of the validation.

In Example 2, the subject matter of Example 1 includes, validating, using processing circuitry of the robotic surgical device, a vertical resection based on the tracked validation position of the optical tracker; wherein the tibiofemoral joint resection includes a tibial plateau resection of the patient tibia, the tibial plateau resection including the horizontal resection and a vertical resection; and wherein the knee arthroplasty validation device includes a partial knee arthroplasty (PKA) validation device, the PKA validation device including a vertical resection validation surface orthogonal to the horizontal resection validation surface, the vertical resection validation surface to contact and validate the vertical resection.

In Example 3, the subject matter of Example 2 includes, validating, using processing circuitry of the robotic surgical device, a PKA flexion gap by comparing a PKA gap validation thickness of the PKA validation device against the PKA flexion gap formed by the patient tibia and the patient femur in flexion; wherein the PKA validation device further includes a substantially planar gap validation surface, the substantially planar gap validation surface substantially parallel to the horizontal resection validation surface and separated from the horizontal resection validation surface by the PKA gap validation thickness, In Example 4, the subject matter of Example 3 includes, validating, using processing circuitry of the robotic surgical device, a PKA extension gap by comparing the PKA gap validation thickness of the PKA validation device against the PKA extension gap formed by the patient tibia and the patient femur in extension.

In Example 5, the subject matter of Example 4 includes, instructing the robotic surgical device to assist in a distal femoral resection of the patient femur corresponding to the patient tibia; disposing the PKA validation device against the distal femoral resection; and instructing the robotic surgical device to validate the distal femoral resection based on a tracked femoral position of the PKA validation device.

In Example 6, the subject matter of Examples 2-5 includes, validating, using processing circuitry of the robotic surgical device, an augment cut validation surface based on the tracked validation position of the optical tracker; wherein the knee arthroplasty validation device includes an augment cut validation device, the augment cut validation device including: a first augment spacer fixedly attached to a first side of the horizontal resection validation surface, the first augment spacer to contact the horizontal resection validation surface; and a second augment spacer fixedly attached to a second side of the horizontal resection validation surface, the second augment spacer to contact the augment cut validation surface.

In Example 7, the subject matter of Examples 1-6 includes, wherein the positioning of the knee arthroplasty validation device includes outputting control instructions to cause the robotic surgical device to position the knee arthroplasty validation device.

In Example 8, the subject matter of Examples 1-7 includes, wherein the positioning of the knee arthroplasty validation device includes a surgeon positioning the knee arthroplasty validation device, the method further including receiving a validation initiation input from the surgeon, the validation initiation input initiating the validation of the horizontal resection.

In Example 9, the subject matter of Examples 1-8 includes, wherein the validation of the horizontal resection validation surface further includes comparing the tracked validation position of the knee arthroplasty validation device against a tracked bone position.

In Example 10, the subject matter of Example 9 includes, wherein the tracked bone position is based on an optical bone position tracker fixedly attached to the patient tibia or the patient femur.

In Example 11, the subject matter of Examples 9-10 includes, wherein the tracked bone position is based on a registration position of a registration pointer, the registration pointer fixedly attached to a robotic arm of the robotic surgical device.

Example 12 is a knee arthroplasty validation system for intraoperative validation of cut surfaces, the system comprising: a robotic surgical device including processing circuitry, the robotic surgical device to assist in a tibiofemoral joint resection of a patient tibia or a patient femur, the tibiofemoral joint resection including a horizontal resection; a knee arthroplasty validation device positioned to contact the horizontal resection, the knee arthroplasty validation device including a horizontal resection validation surface and an optical tracker fixedly attached to the knee arthroplasty validation device; and an optical tracker fixedly attached to the knee arthroplasty validation device; wherein processing circuitry of the robotic surgical device validates the horizontal resection validation surface based on a tracked validation position of the optical tracker and triggers an update of a display to indicate completion of the validation.

In Example 13, the subject matter of Example 12 includes, the processing circuitry of the robotic surgical device further to validate a vertical resection based on the tracked validation position of the optical tracker; wherein the tibiofemoral joint resection includes a tibial plateau resection of a patient tibia, the tibial plateau resection including the horizontal resection and a vertical resection; and wherein the knee arthroplasty validation device includes a partial knee arthroplasty (PKA) validation device, the PKA validation device including a vertical resection validation surface orthogonal to the horizontal resection validation surface, the vertical resection validation surface to contact and validate the vertical resection.

In Example 14, the subject matter of Example 13 includes, the processing circuitry of the robotic surgical device further to validate, using processing circuitry of the robotic surgical device, a PKA flexion gap by comparing a PKA gap validation thickness of the PKA validation device against the PKA flexion gap formed by the patient tibia and the patient femur in flexion; wherein the PKA validation device further includes a substantially planar gap validation surface, the substantially planar gap validation surface substantially parallel to the horizontal resection validation surface and separated from the horizontal resection validation surface by the PKA gap validation thickness.

In Example 15, the subject matter of Example 14 includes, wherein the substantially planar gap validation surface validates a PKA extension gap by comparing the PKA gap validation thickness of the PKA validation device against the PKA extension gap formed by the patient tibia and the patient femur in extension.

In Example 16, the subject matter of Example 15 includes, wherein in response to receipt of control instructions, the robotic surgical device is further to: assist in a distal femoral resection of patient femur corresponding to the patient tibia; and validate the distal femoral resection based on a tracked femoral position of the PKA validation device disposed against the distal femoral resection.

In Example 17, the subject matter of Examples 12-16 includes, the processing circuitry of the robotic surgical device further to validate, using processing circuitry of the robotic surgical device, an augment cut validation surface based on the tracked validation position of the optical tracker; wherein the knee arthroplasty validation device includes an augment cut validation device, the augment cut validation device including: a first augment spacer fixedly attached to a first side of the horizontal resection validation surface, the first augment spacer to contact the horizontal resection validation surface; and a second augment spacer fixedly attached to a second side of the horizontal resection validation surface, the second augment spacer to contact the augment cut validation surface.

In Example 18, the subject matter of Examples 12-17 includes, wherein in response to receipt of control instructions, the control instructions further cause the robotic surgical device to position the knee arthroplasty validation device.

In Example 19, the subject matter of Examples 12-18 includes, wherein the positioning of the knee arthroplasty validation device includes a surgeon positioning the knee arthroplasty validation device, the processing circuitry of the robotic surgical device further to receive a validation initiation input from the surgeon, the validation initiation input initiating the validation of the horizontal resection.

In Example 20, the subject matter of Examples 12-19 includes, wherein the validation of the horizontal resection validation surface further includes comparing the tracked validation position of the knee arthroplasty validation device against a tracked bone position.

In Example 21, the subject matter of Example 20 includes, an optical bone position tracker fixedly attached to the patient tibia or the patient femur, wherein the tracked bone position is based on the optical bone position tracker.

In Example 22, the subject matter of Examples 20-21 includes, a registration pointer fixedly attached to a robotic arm of the robotic surgical device, wherein the tracked bone position is based on a registration position of a registration pointer.

Example 23 is at least one non-transitory machine-readable storage medium, comprising a plurality of instructions that, responsive to being executed with processor circuitry of a computer-controlled device, cause the computer-controlled device to: output control instructions to cause a robotic surgical device to assist in a tibiofemoral joint resection of a patient tibia or a patient femur, the tibiofemoral joint resection including a horizontal resection; position a knee arthroplasty validation device to contact the horizontal resection, the knee arthroplasty validation device including a horizontal resection validation surface and an optical tracker fixedly attached to the knee arthroplasty validation device; validate, using processing circuitry of the robotic surgical device, the horizontal resection based on a tracked validation position of the optical tracker; and trigger an update of a display to indicate completion of the validation.

In Example 24, the subject matter of Example 23 includes, the instructions further causing the computer-controlled device to validate, using processing circuitry of the robotic surgical device, a vertical resection based on the tracked validation position of the optical tracker; wherein the tibiofemoral joint resection includes a tibial plateau resection of the patient tibia, the tibial plateau resection including the horizontal resection and a vertical resection; and wherein the knee arthroplasty validation device includes a partial knee arthroplasty (PKA) validation device, the PKA validation device including a vertical resection validation surface orthogonal to the horizontal resection validation surface, the vertical resection validation surface to contact and validate the vertical resection.

in Example 25, the subject matter of Example 24 includes, the instructions further causing the computer-controlled device to validate, using processing circuitry of the robotic surgical device, a PKA flexion gap by comparing a PKA gap validation thickness of the PKA validation device against the PKA flexion gap formed by the patient tibia and the patient femur in flexion; wherein the PKA validation device further includes a substantially planar gap validation surface, the substantially planar gap validation surface substantially parallel to the horizontal resection validation surface and separated from the horizontal resection validation surface by the PKA gap validation thickness.

In Example 26, the subject matter of Example 25 includes, the instructions further causing the computer-controlled device to validate, using processing circuitry of the robotic surgical device, a PKA extension gap by comparing the PKA gap validation thickness of the PKA validation device against the PKA extension gap formed by the patient tibia and the patient femur in extension.

In Example 27, the subject matter of Example 26 includes, instructing the robotic surgical device to assist in a distal femoral resection of the patient femur corresponding to the patient tibia; disposing the PKA validation device against the distal femoral resection; and instructing the robotic surgical device to validate the distal femoral resection based on a tracked femoral position of the PKA validation device.

In Example 28, the subject matter of Examples 24-27 includes, the instructions further causing the computer-controlled device to validate, using processing circuitry of the robotic surgical device, an augment cut validation surface based on the tracked validation position of the optical tracker; wherein the knee arthroplasty validation device includes an augment cut validation device, the augment cut validation device including: a first augment spacer fixedly attached to a first side of the horizontal resection validation surface, the first augment spacer to contact the horizontal resection validation surface; and a second augment spacer fixedly attached to a second side of the horizontal resection validation surface, the second augment spacer to contact the augment cut validation surface.

In Example 29, the subject matter of Examples 23-28 includes, wherein the positioning of the knee arthroplasty validation device includes outputting control instructions to cause the robotic surgical device to position the knee arthroplasty validation device.

In Example 30, the subject matter of Examples 23-29 includes, wherein the positioning of the knee arthroplasty validation device includes a surgeon positioning the knee arthroplasty validation device, the instructions further causing the computer-controlled device to receive a validation initiation input from the surgeon, the validation initiation input initiating the validation of the horizontal resection.

In Example 31, the subject matter of Examples 23-30 includes, wherein the validation of the horizontal resection validation surface further includes comparing the tracked validation position of the knee arthroplasty validation device against a tracked bone position.

In Example 32, the subject matter of Example 31 includes, wherein the tracked bone position is based on an optical bone position tracker fixedly attached to the patient tibia or the patient femur.

In Example 33, the subject matter of Examples 31-32 includes, wherein the tracked bone position is based on a registration position of a registration pointer, the registration pointer fixedly attached to a robotic arm of the robotic surgical device.

Example 34 is a knee arthroplasty validation apparatus for intraoperative validation of cut surfaces, the apparatus comprising: means for outputting control instructions to cause a robotic surgical device to assist in a tibiofemoral joint resection of a patient tibia or a patient femur, the tibiofemoral joint resection including a horizontal resection; means for positioning a knee arthroplasty validation device to contact the horizontal resection, the knee arthroplasty validation device including a horizontal resection validation surface and an optical tracker fixedly attached to the knee arthroplasty validation device; means for validating, using processing circuitry of the robotic surgical device, the horizontal resection based on a tracked validation position of the optical tracker; and means for triggering an update of a display to indicate completion of the validation.

In Example 35, the subject matter of Example 34 includes, means for validating, using processing circuitry of the robotic surgical device, a vertical resection based on the tracked validation position of the optical tracker; wherein the tibiofemoral joint resection includes a tibial plateau resection of the patient tibia, the tibial plateau resection including the horizontal resection and a vertical resection; and wherein the knee arthroplasty validation device includes a partial knee arthroplasty (PKA) validation device, the PKA validation device including a vertical resection validation surface orthogonal to the horizontal resection validation surface, the vertical resection validation surface to contact and validate the vertical resection.

In Example 36, the subject matter of Example 35 includes, means for validating, using processing circuitry of the robotic surgical device, a PKA flexion gap by comparing a PKA gap validation thickness of the PKA validation device against the PKA flexion gap formed by the patient tibia and the patient femur in flexion; wherein the PKA validation device further includes a substantially planar gap validation surface, the substantially planar gap validation surface substantially parallel to the horizontal resection validation surface and separated from the horizontal resection validation surface by the PKA gap validation thickness.

In Example 37, the subject matter of Example 36 includes, means for validating, using processing circuitry of the robotic surgical device, a PKA extension gap by comparing the PKA gap validation thickness of the PKA validation device against the PKA extension gap formed by the patient tibia and the patient femur in extension.

In Example 38, the subject matter of Example 37 includes, means for instructing the robotic surgical device to assist in a distal femoral resection of the patient femur corresponding to the patient tibia; means for disposing the PKA validation device against the distal femoral resection; and means for instructing the robotic surgical device to validate the distal femoral resection based on a tracked femoral position of the PKA validation device.

In Example 39, the subject matter of Examples 35-38 includes, means for validating, using processing circuitry of the robotic surgical device, an augment cut validation surface based on the tracked validation position of the optical tracker; wherein the knee arthroplasty validation device includes an augment cut validation device, the augment cut, validation device including: a first augment spacer fixedly attached to a first side of the horizontal resection validation surface, the first augment spacer to contact the horizontal resection validation surface; and a second augment spacer fixedly attached to a second side of the horizontal resection validation surface, the second augment spacer to contact the augment cut validation surface.

In Example 40, the subject matter of Examples 34-39 includes, wherein the means for positioning of the knee arthroplasty validation device includes means for outputting control instructions to cause the robotic surgical device to position the knee arthroplasty validation device.

In Example 41, the subject matter of Examples 34-40 includes, wherein the means for positioning of the knee arthroplasty validation device includes a surgeon positioning the knee arthroplasty validation device, the apparatus further including means for receiving a validation initiation input from the surgeon, the validation initiation input initiating the validation of the horizontal resection.

In Example 42, the subject matter of Examples 34-41 includes, wherein the validation of the horizontal resection validation surface further includes means for comparing the tracked validation position of the knee arthroplasty validation device against a tracked bone position.

In Example 43, the subject matter of Example 42 includes, wherein the tracked bone position is based on an optical bone position tracker fixedly attached to the patient tibia or the patient femur.

In Example 44, the subject matter of Examples 42-43 includes, wherein the tracked bone position is based on a registration position of a registration pointer, the registration pointer fixedly attached to a robotic arm of the robotic surgical device.

Example 45 is at least one machine-readable medium including instructions that, when executed by processing circuitry, cause the processing circuitry to perform operations to implement of any of Examples 1-44.

Example 46 is an apparatus comprising means to implement of any of Examples 1-44.

Example 47 is a system to implement of any of Examples 1-44.

Example 48 is a method to implement of any of Examples 1-44.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A knee arthroplasty validation system for intraoperative validation of cut surfaces, the system comprising:
    a robotic surgical device including processing circuitry, the robotic surgical device to assist in a tibiofemoral joint resection of a patient tibia or a patient femur, the tibiofemoral joint resection including a horizontal resection and a vertical resection;
    a solid knee arthroplasty validation device positioned to contact the horizontal resection and the vertical resection, the solid knee arthroplasty validation device including a horizontal resection validation surface, a top validation surface opposite from the horizontal resection validation surface, a vertical resection validation surface orthogonal to the horizontal resection validation surface, the vertical resection validation surface to contact and validate the vertical resection, a distal portion to validate a posterior tibial plateau resection gap, a proximate portion to validate an anterior tibial plateau resection gap, and an anterior stop configured to rest against a tibial anterior cortex of the patient tibia; and
    an optical tracker fixedly attached to the proximate portion of the solid knee arthroplasty validation device;
    wherein the knee arthroplasty validation device includes a gap validation thickness between the top validation surface and the horizontal resection validation surface, the gap validation thickness being different in the proximate portion from the distal portion;
    wherein the processing circuitry of the robotic surgical device validates the vertical resection validation surface, the posterior tibial plateau resection gap, and the anterior tibial plateau resection gap based on a tracked validation position of the optical tracker and triggers an update on a display to indicate completion of the validation.

2. The system of claim 1, wherein the tibiofemoral joint resection includes a tibial plateau resection of a patient tibia, the tibial plateau resection including the horizontal resection and the vertical resection; and
    wherein the solid knee arthroplasty validation device includes a partial knee arthroplasty (PKA) validation device, the PKA validation device including the vertical resection validation surface.

3. The system of claim 2, the processing circuitry of the robotic surgical device further to validate, using the processing circuitry of the robotic surgical device, a PKA flexion gap by comparing a PKA gap validation thickness of the PKA validation device against the PKA flexion gap formed by the patient tibia and the patient femur in flexion;
    wherein the PKA validation device further includes a substantially planar gap validation surface, the substantially planar gap validation surface substantially parallel to the horizontal resection validation surface and separated from the horizontal resection validation surface by the PKA gap validation thickness.

4. The system of claim 3, wherein the substantially planar gap validation surface validates a PKA extension gap by comparing the PKA gap validation thickness of the PKA validation device against the PKA extension gap formed by the patient tibia and the patient femur in extension.

5. The system of claim 4, wherein in response to receipt of control instructions, the robotic surgical device is further to:
    assist in a distal femoral resection of patient femur corresponding to the patient tibia; and
    validate the distal femoral resection based on a tracked femoral position of the PKA validation device disposed against the distal femoral resection.

6. The system of claim 2, wherein the processing circuitry further validates, using the gap validation thickness, a flexion gap formed between the tibial plateau resection and a corresponding resected surface of the patient femur when a patient knee is in flexion.

7. The system of claim 6, wherein the processing circuitry further validates, using the gap validation thickness, an extension gap formed between the tibial plateau resection and the corresponding resected surface of the patient femur when the patient knee is in extension.

8. The system of claim 1, wherein the processing circuitry further validates the horizontal resection by determining a horizontal resection depth and a horizontal resection slope based on the tracked validation position.

9. The system of claim 1, wherein the processing circuitry further determines a location of a tibial posterior cortex of the patient tibia using a length of the arthroplasty validation device.

10. The system of claim 6, wherein the solid knee arthroplasty validation device includes:
    a proximate portion, the optical tracker fixedly attached to the proximate portion; and
    a distal portion opposite from the proximate portion, the gap validation thickness associated with the distal portion.

* * * * *